US012653641B2

(12) United States Patent
Mückner

(10) Patent No.: US 12,653,641 B2
(45) Date of Patent: Jun. 16, 2026

(54) SURGICAL TOOL AND HANDHELD ELECTROSURGICAL INSTRUMENT, AND METHOD FOR RECOGNIZING A SURGICAL TOOL

(71) Applicant: OLYMPUS WINTER & IBE GMBH, Hamburg (DE)

(72) Inventor: Andreas Mückner, Schwarzenbek (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 468 days.

(21) Appl. No.: 18/136,371

(22) Filed: Apr. 19, 2023

(65) Prior Publication Data

US 2023/0404704 A1 Dec. 21, 2023

Related U.S. Application Data

(60) Provisional application No. 63/352,715, filed on Jun. 16, 2022.

(51) Int. Cl.
*A61B 90/98* (2016.01)
*A61B 18/12* (2006.01)
*A61B 18/14* (2006.01)
*A61B 18/00* (2006.01)

(52) U.S. Cl.
CPC ........... *A61B 90/98* (2016.02); *A61B 18/149* (2013.01); *A61B 2018/00178* (2013.01); *A61B 2018/00875* (2013.01); *A61B 2018/0091* (2013.01); *A61B 2018/1253* (2013.01); *A61B 2018/126* (2013.01); *A61B 18/1485* (2013.01)

(58) Field of Classification Search
CPC .... A61B 90/98; A61B 18/149; A61B 18/1485
See application file for complete search history.

(56) References Cited

U.S. PATENT DOCUMENTS

| | | | |
|---|---|---|---|
| 3,790,736 A | | 2/1974 | Matsumura et al. |
| 6,074,386 A | | 6/2000 | Goble et al. |
| 6,366,206 B1 * | | 4/2002 | Ishikawa ................ A61B 90/98 |
| | | | 604/362 |
| 2009/0112204 A1 | | 4/2009 | Aronow et al. |
| 2015/0083781 A1 * | | 3/2015 | Giordano ....... A61B 17/320092 |
| | | | 227/176.1 |
| 2015/0335379 A1 * | | 11/2015 | Edwards ........ A61B 17/320016 |
| | | | 606/171 |
| 2018/0228528 A1 * | | 8/2018 | Fraasch .............. A61B 18/1206 |
| 2018/0256287 A1 * | | 9/2018 | Bosisio .................... A61C 5/42 |

(Continued)

FOREIGN PATENT DOCUMENTS

| | | |
|---|---|---|
| JP | S49-64038 A | 6/1974 |
| JP | H08-124704 A | 5/1996 |
| JP | 2001-112774 A | 4/2001 |

(Continued)

*Primary Examiner* — Sean W Collins
(74) *Attorney, Agent, or Firm* — Oliff PLC

(57) ABSTRACT

A surgical tool, which can be identified in a simple and at the same time unambiguous manner. This is achieved in that a surgical tool has an electrical conductor element having a tool-specific electronic signature. An unambiguous identification of the tool is possible via this tool-specific electronic signature. Each surgical tool of the claimed type thus has a signature, using which it can be unambiguously identified.

8 Claims, 3 Drawing Sheets

(56)                    References Cited

U.S. PATENT DOCUMENTS

Figure 1:
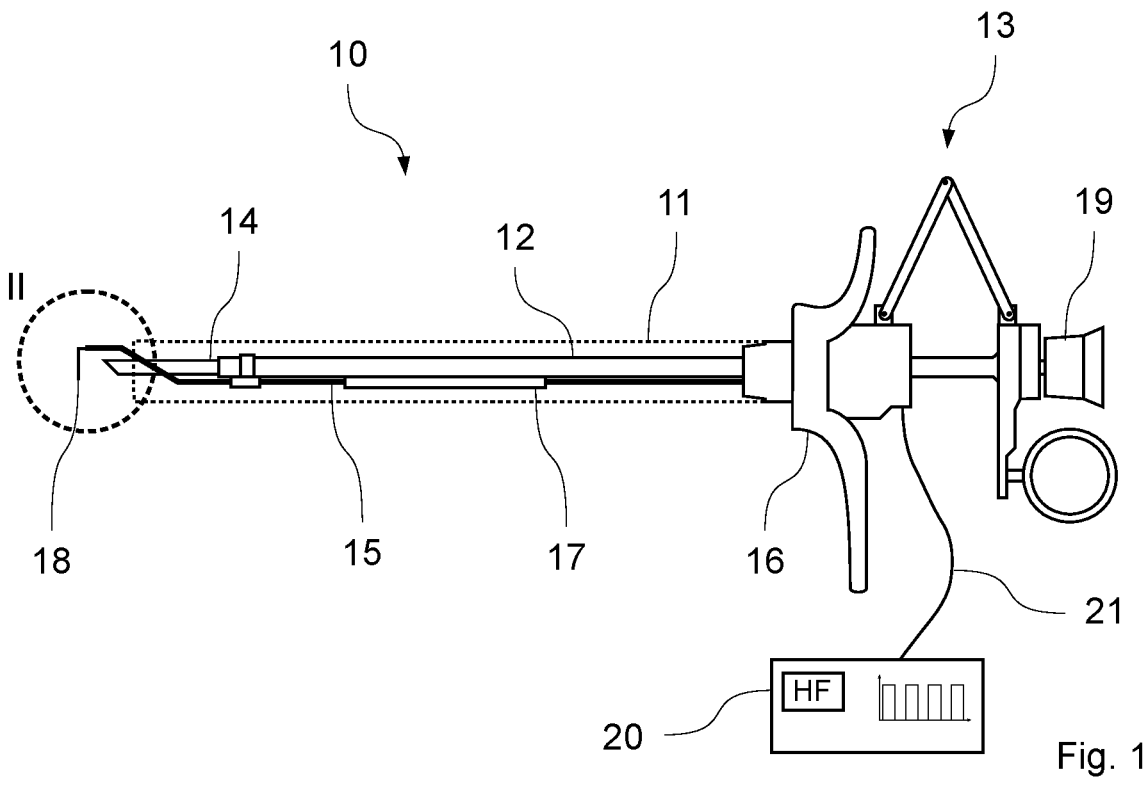

| | | | |
|---|---|---|---|
| 2020/0129264 A1* | 4/2020 | Oñativia Bravo ..... | A61B 90/39 |
| 2020/0410180 A1* | 12/2020 | Shelton, IV ........... | A61B 17/10 |

FOREIGN PATENT DOCUMENTS

| | | | |
|---|---|---|---|
| JP | 2008-212638 | A | 9/2008 |
| JP | 2009-531769 | A | 9/2009 |
| JP | 2011-519636 | A | 7/2011 |
| JP | 2012-187408 | A | 10/2012 |
| JP | 2016-182521 | A | 10/2016 |
| JP | 2017-033101 | A | 2/2017 |
| JP | 6167111 | B2 | 7/2017 |
| JP | 2017-175485 | A | 9/2017 |
| JP | 2017-533736 | A | 11/2017 |
| JP | 2019-180606 | A | 10/2019 |
| JP | 2022-514481 | A | 2/2022 |
| WO | 2007/113722 | A1 | 10/2007 |
| WO | 2009/074329 | A2 | 6/2009 |
| WO | 2009/137421 | A1 | 11/2009 |
| WO | 2016/030178 | A1 | 3/2016 |
| WO | 2020/121085 | A1 | 6/2020 |

* cited by examiner

SURGICAL TOOL AND HANDHELD ELECTROSURGICAL INSTRUMENT, AND METHOD FOR RECOGNIZING A SURGICAL TOOL

The invention relates to a surgical tool. Furthermore, the invention relates to a handheld electrosurgical instrument and a method for recognising a surgical tool.

Handheld electrosurgical instruments, in particular resectoscopes, of the type described here are preferably used for treatment in the area of the bladder, in particular in the area of the prostate. The field of use of these instruments is not restricted to these areas, however, but rather also comprises the treatment of other organs, which are preferably arranged in the human abdomen.

The handheld instruments or resectoscopes typically have an elongated shaft, which is inserted into the body of the patient, for the treatment of the diseased organs. Different surgical tools can be coupled to a distal end of the shaft. Thus, for example, a resectoscope for high-frequency surgery has an electrode to which high-frequency alternating current can be applied. This electrode is fastened to a distal end of a shaft-type electrode carrier for operation. Surgical electrodes of the type described here can have, for example, the form of a loop, a ball, a hemisphere, or the like. The electrode can be contacted via a corresponding electrode contact with a high-frequency source or an HF generator via an electrical conductor at a proximal end of the electrode or the shaft of the resectoscope.

Various carriers for use on monopolar or bipolar resectoscopes are known from the prior art. In bipolar resectoscopes, both poles of the high-frequency generator are possibly connected to the resectoscope or to the carrier. In addition to the HF line or HF electrode or active electrode transmitting the high-frequency current, a neutral conductor or a back electrode or a back conductor is provided on the resectoscope, which returns or discharges into the high-frequency source the current flowing back after the introduction into the tissue to be treated. The electrical contacting of the active electrode and the neutral electrode can be carried out by two separate cables, or alternatively by a Y-cable or by a two-ended breakout cable, which is connectable to the HF generator, or by a two-wire cable having both contacts on a plug.

The tools for high-frequency surgery or high-frequency tools or surgical tools, in particular the electrode, can be coupled or locked with the carrier or on the slide. The electrodes are often so-called single-use instruments or disposable electrodes, which have to be replaced after each treatment. Up to this point, such electrodes have been identified with a batch number, but cannot be unambiguously identified in this way. A tool identifier directly on or in the electrode, via which it is recognizable whether the electrode used is an electrode compatible with the instrument or which type of electrode it is, and whether this electrode has already been used, is not known from the prior art. In particular an unambiguous identification of the electrode can be very helpful for both the production of the tool and for the application. Thus, for example, an impermissible multiple use could be recognized and avoided by an unambiguous identification of a tool. Means for unambiguous identification of objects from other fields of technology are not applicable due to the requirements which are placed on medical instruments and due to the dimensioning. Thus, for example, a barcode represents a practical option for unambiguously identifying objects and unambiguously identifying them by way of a corresponding read device. Such a solution proves to be completely unsuitable for the tools described here. In addition to the restricted space on the tool, reading out a miniaturized barcode would prove to be difficult to implement technically.

Proceeding therefrom, the invention is based on the object of providing a surgical tool, a handheld electrosurgical instrument, and a method for recognizing a surgical tool, using which surgical tools may be identified in a simple and unambiguous manner.

It is accordingly provided that a surgical tool has an electrical conductor element having a tool-specific electronic signature. An unambiguous identification of the tool is possible via this tool-specific electronic signature. Each surgical tool of the claimed type thus has a signature, using which it can be unambiguously identified. Since the surgical tool can be electrically contacted for the handheld electrosurgical instrument, the signature, which is provided by the electrical conductor element of the tool, may be read out in a simple manner. Not only the type, the model, and the individual tool may be recognized by this unambiguous identification, but also whether this tool was already used and possibly was prepared. A multiple use of the tool, which is impermissible from a technical aspect, can thus be avoided, thereby also increasing the level of safety for the patient during the operation.

It can preferably be provided that the electrical conductor element is arranged directly on the tool and is preferably integrated in an outer wall. Known tools of the type described here have a wire or a rod-like conductor at least in some areas. It is conceivable that the electrical conductor element is arranged on the outer wall of this wire. If the tool has any plate-like shapes or flat surfaces, the electrical conductor element can also be arranged thereon. Similarly, it is conceivable that the electrical conductor element is integrated in the tool, for example, by the use of different materials having different electrical properties or conductivities or resistances.

In particular, it is conceivable that the electrical conductor element is integrated in an electrical line for supplying the tool with electrical energy or is in contact with this line. It is thus entirely conceivable that the electrical conductor has a line, in particular an internal line, in which the claimed electrical conductor element is integrated and which permits an unambiguous identification of the tool. Similarly, it is conceivable that the electrical conductor element is in electrical contact with the conductor for supplying the tool, preferably the supply line. This has proven to be particularly advantageous since the tool is to be supplied with electrical energy in any case and is in direct contact with an HF generator. A contactless, i.e., capacitive or inductive, coupling of the electrical conductor element with the supply conductor is also conceivable. The unambiguous identification of the tool takes place inductively or capacitively in this case via the supply line or the cable to the HF generator.

A further exemplary embodiment can preferably be that the electrical conductor element has a meandering structure, wherein the structure consists of an individual number of loops, preferably having different lengths and/or distances, and thus receives a tool-specific electronic signature, by which an unambiguous identification of the tool is possible. By changing the number of the loops and/or the lengths and distances of the individual loops of a meander for each individual tool, this tool may be unambiguously identified. The unambiguous identification which results due to the characteristic electrical properties is determined during the production of the tool and stored in a database. The operator receives these items of information with the purchase of the tool. Upon use of the tool, the data are input manually or automatically by an operating device, which can be, for example, the HF generator.

A further exemplary embodiment of the invention can provide that the electrical conductor element is formed as an embossing, preferably an individual embossing, on the tool and thus receives a tool-specific electronic signature, by which an unambiguous identification of the tool is possible. Electrical properties, such as an electrical resistance or the impedance, may be changed by the embossing of the tool. These changed electrical properties may be read out and identified. The identified properties or the signature can then be compared to a database, in which the signatures of all tools are stored. A plurality of different electronic signatures for a corresponding plurality of tools may be produced by slight variations of the embossing. It has been shown that extremely small variations of the embossing result in different electronic properties or signatures.

In addition, it represents a further possible embodiment of the invention that the electrical conductor element is designed as an antenna having a preferably individual emission characteristic and thus receives a tool-specific electronic signature, by which an unambiguous identification of the tool is possible. This antenna can receive, for example, electromagnetic waves from the handheld electrosurgical instrument or the HF generator. Due to the small size of the tool, which can be a few millimeters, the antenna is to be dimensioned accordingly. Therefore, waves in the terahertz range come into consideration as incoming and outgoing electromagnetic radiation. Due to the individual structuring of the antenna, it emits a signal after excitation which can represent an unambiguous electronic signature. Since the transmission and reception of such radiation is known, such an identification of the surgical tool proves to be particularly simple and well integratable into existing systems.

Furthermore, a particularly advantageous exemplary embodiment is that the electrical conductor element is designed as a chipless RFID element. Such RFID elements are particularly inexpensive, easily producible, and able to be miniaturized. Such an element could thus be applied, for example, by means of laser technology by corresponding structuring on the tool. Ultimately, the chipless RFID element also represents an electrically conductive element, which receives signals like an antenna and emits them again in a modified manner. Since these types of components are passive, no further energy storage devices are necessary. Due to a direct integration of the conductor element into the tool, this could also be prepared, specifically without influencing the properties of the conductor element.

A handheld electrosurgical instrument to achieve the object mentioned at the outset is described. It is accordingly provided that the handheld instrument has a tool. This tool can be detachably coupled with a proximal end to a distal end of a toolholder, in particular an electrode carrier, of the handheld electrosurgical instrument. In addition, the handheld electrosurgical instrument is connectable to an HF generator, in order to supply the tool with a high frequency AC voltage.

One preferred exemplary embodiment of the handheld electrosurgical instrument can provide that the toolholder has a coil, preferably an antenna, through which an electromagnetic pulse, in particular an excitation signal, can be emitted via a control unit, preferably the HF generator. This coil is located in direct proximity to the tool. The tool can have a corresponding conductor element or a coil as a counter element to the coil. Due to the direct proximity between the coil and the tool, only a small transmission power is necessary to generate electromagnetic waves, which can be received by the electrical 10 conductor element on the tool. After excitation of the electrical conductor element or the coil on the tool by the electromagnetic waves of the toolholder, an outgoing signal is generated by the tool, which is received either by the HF generator or the coil of the toolholder. A tool-specific electronic signature of the electrical conductor element of the tool may be unambiguously identified. For this purpose, the outgoing signal of the tool is to be analyzed 15 by the control unit. The spectrum of the signal represents an electronic fingerprint of the tool, which can be compared to a database stored in the control unit.

A method for recognizing a surgical tool to achieve the above-mentioned object is described. It is accordingly provided that a surgical tool is recognized for a handheld electrosurgical instrument. The invention provides that at least one electromagnetic pulse, in particular an excitation signal, is generated by an HF generator connected to the handheld instrument, which pulse is received by an electrical conductor element of the tool and is reflected or emitted again as a characteristic or individual outgoing signal, wherein the outgoing signal is received by the HF generator. The signal generated by the HF generator is matched to the electrical conductor element. Depending on the type of the electrical conductor element, the excitation signal can be an electrical pulse or an electric current or an electromagnetic wave. It is similarly conceivable that a plurality of successive pulses having a specific pulse width is emitted by the HF generator. The signal reflected or returned or emitted by the electrical conductor element has a specific or characteristic spectrum. This signal is received and analyzed by a corresponding read unit or antenna of the HF generator. For example, the individual signature of the tool may be recognized by a spectral analysis.

The outgoing or reflected signal of the tool received by the HF generator is compared to reference data, which are stored on a database. These reference data are stored recognition data of the tools used. It may thus be recognized directly which tool it is. In dependence on the stored data, on the one hand, operating parameters, such as for example the operating voltage, of the tool may be set automatically. The operator similarly recognizes whether this tool has already been used and/or has been prepared. Special exemplary embodiments can also provide that the data stored on the electrical conductor element are changed, for example, to mark a further use of the tool.

One preferred exemplary embodiment of the invention can provide that the at least one electromagnetic pulse is supplied via an electrical supply conductor, in particular a cable, to the electrical conductor element of the tool, and that the reflected signal is received and analyzed at the electrical conductor element, which can preferably be an embossing, a meandering structure, or a chipless RFID.

A further advantageous exemplary embodiment of the method can provide that a method of time domain reflectometry (TDR) is used to determine the characteristic properties of the electrical conductor element of the tool and to assign them to a specific tool. Precise statements about the properties of the conductor element may be derived from the electrical pulses received in the time interval, which are reflected at the electrical conductor element. These properties, which are individual for each conductor structure, suggest themselves for the unambiguous identification of the tool. Extremely small variations in the conductor structure or in the type of the conductor element may be determined by the TDR in a precise manner.

Furthermore, it is conceivable that at least one electromagnetic pulse is applied to a coil or an antenna of the handheld electrosurgical instrument and that an electromagnetic signal is emitted by the coil or the antenna, which is received by the electrical conductor element and emitted again. The coil or the antenna of the handheld instrument is either in direct contact with the electrical conductor to the HF generator or is also excited via electromagnetic waves by the HF generator. The properties of the electromagnetic pulses or waves may be set as needed via a control unit of the HF generator. The signals emitted by the conductor element are in turn received and analyzed by the control unit of the HF generator. The items of information transported in the signal may be read out by a spectral analysis, for example.

Figure 2:
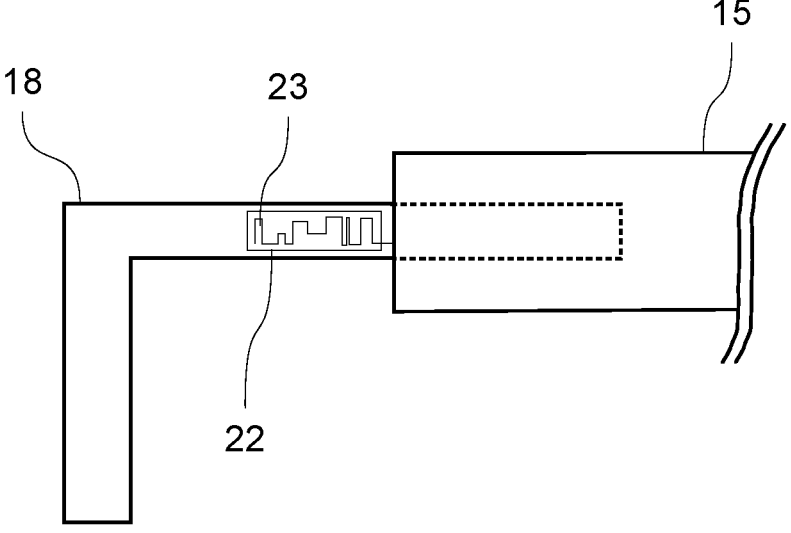
Figure 3:
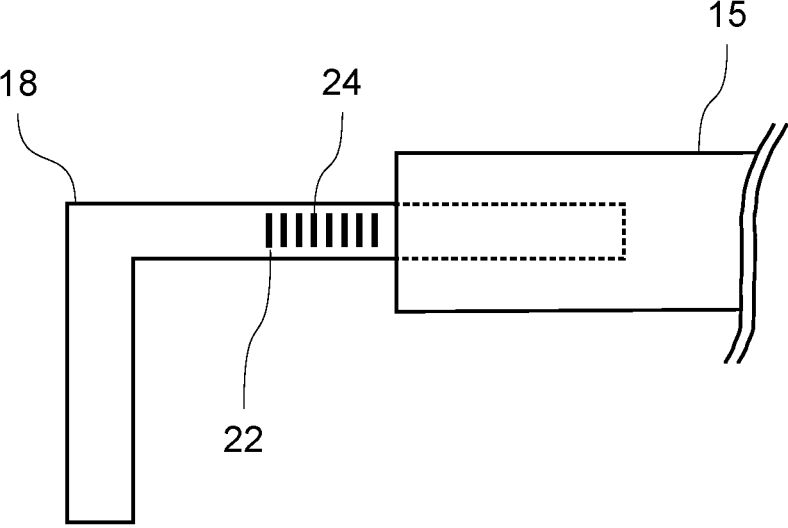
Figure 4:
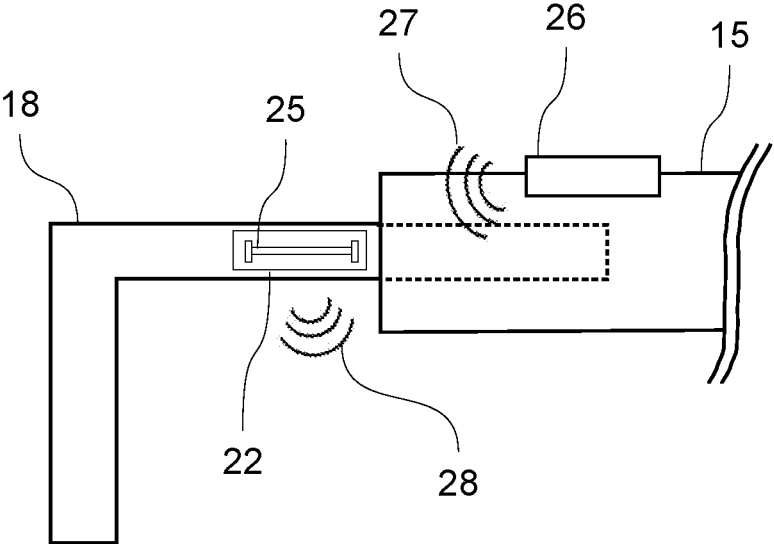
Figure 5:
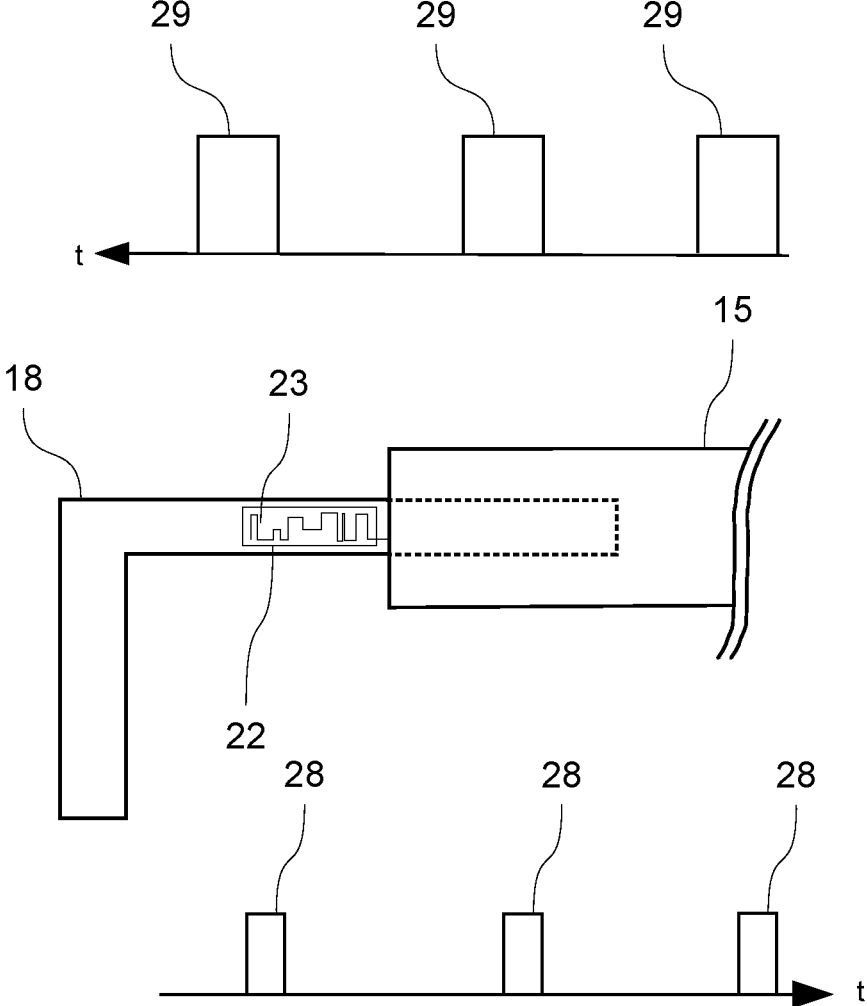

A preferred exemplary embodiment of a resectoscope for high-frequency surgery will be described in more detail hereinafter on the basis of the drawings. In the figures:

FIG. 1 shows a schematic illustration of an HF resectoscope having a surgical tool, FIG. 2 shows a detail enlargement of the tool having an electrical conductor element, FIG. 3 shows a detail enlargement of the tool having a further exemplary embodiment of an electrical conductor element, FIG. 4 shows a detail enlargement of the tool having a further exemplary embodiment of an electrical conductor element, and FIG. 5 shows an illustration of a method for recognizing the tool according to FIG. 2.

A resectoscope 10 is shown as an example of a handheld electrosurgical instrument in FIG. 1. Such resectoscopes 10 essentially consist of a carrier 13, to which an inner tube 12 and a shaft 11 can be detachably coupled. Both an optical unit 14 and an electrode carrier 15 can be arranged in the inner tube 12. In the exemplary embodiment shown here, the electrode carrier 15 is positioned on an outer wall of the inner tube 12. The optical unit 14 extends over the entire length of the resectoscope 10. In known embodiments, the optical unit 14 is formed by an optical fiber or a rod lens system. It enables the operator to observe the area in front of the distal end of the resectoscope 10 by means of an eyepiece 19 positioned proximally on the carrier 13.

A surgical tool is detachably fastened at a distal end of the electrode carrier 15. In the exemplary embodiment shown here, the tool is designed as a loop-type electrode 18. However, it is also conceivable that another tool is fastened on the electrode carrier 17 or the electrode 18 has a different shape. The electrode 18 is connected via the electrode carrier 15 to the slide 16. The slide 16 may be moved translationally along the inner tube 12. The electrode 18 can be guided through the tissue to be manipulated by this movement along a longitudinal axis of the resectoscope 10. By applying an HF voltage to the electrode 18, the manipulation of the tissue is carried out. For stable mounting and movement of the electrode carrier 15 along the inner tube 12, it is supported and stabilized by guide elements 17.

The electrical energy or the HF voltage for the operation of the electrode 18 is provided by a generator 20. This HF generator 20 is connected to the instrument or the resectoscope 10 or the carrier 13 via an electrical line 21. This electrical line 21 is typically connected via a plug connection to the carrier 13. In a bipolar resectoscope 10, the electrode 18 is connected via two electrical conductors 21 to the generator 20, namely using an HF line and a neutral conductor or a neutral electrode. In a monopolar resectoscope 10, the neutral electrode is formed, for example, by the body of the patient. For further details with respect to the mode of operation and the structure of a resectoscope 10 of the type described here, reference is made to the relevant prior art.

According to the invention, each individual electrode 18 is equipped with an electrical conductor element 22 for the recognition or identification of the electrode 18. This electrical conductor element 22 is individual and unique for each electrode 18. Each electrode 18 may thus be unambiguously identified. A detail enlargement of the distal end of the resectoscope 10 is shown in FIG. 2. The electrode 18 is inserted with a proximal end into the distal end of the electrode carrier 15 here. The electrode 18 is mechanically and electrically coupled to the electrode carrier 15 by this plug connection. The electrode 18 is only electrically connected to an inner conductor (not shown) of the electrode carrier 15, whereas the outer wall of the electrode carrier 15 is electrically insulated from the electrode 18.

A possible embodiment of an electrical conductor element 22 is shown very schematically and by way of example on the electrode 18 shown in FIG. 2. This can be an electrical conductor structure 23 which is either arranged directly on the surface of the electrode 18 or is insulated by an insulator from the electrode 18. The conductor structure 23 shown here by way of example represents a meander made up of multiple loops having various lengths and widths. Each conductor structure 23 has individual electronic properties due to variation of the number of the loops and due to variation of the lengths and widths of these loops.

The electrical conductor element 22 is electrically connected to the HF generator 20 via the electrode carrier 15. Since the electrical conductor structure 23 of the electrical conductor element 22 has a tool-specific and characteristic form, it also has unique electrical properties, such as a characteristic electrical resistance. This electrical resistance is determinable via the electrical line 21 and the generator 20. For this purpose, the HF generator 20 has a corresponding control unit and a corresponding measuring device. The determination of the electrical resistance can take place, for example, during the operation of the resectoscope 10 or detached therefrom. For example, it is conceivable that before beginning the operative intervention, the electrode 18 is inserted into the electrode carrier 15 and the electrical conductor element 22 is read out by the generator 20. The control unit of the generator 20 can have a database in which the electrical signatures of all available tools or electrodes 18 are stored. The operator learns by a data comparison which electrode 18 it is and which data are stored for this electrode 18.

In a further exemplary embodiment of the invention, the electrode 18 according to FIG. 3 has an individual embossing 24. The electrical properties of the electrode 18 are slightly changed by this embossing 24, by which a tool-specific electronic signature results. This signature may be read out, precisely as described above in the exemplary embodiment according to FIG. 2, by a control unit or a measuring unit of the generator 20. A plurality of different embossed signatures for the unambiguous identification of the electrodes 18 can be carried out by a change of the embossing 24, for example by variation of the shape and the number of the individual embossed patterns. This embodiment of the claimed electrical conductor element 22 is particularly advantageous, since it can be performed without great effort directly on the electrode 18. The electrode 18 can also be unambiguously identified in this exemplary embodiment by a data comparison due to corresponding storage of the electrical properties of the electrode 18 in a database of the generator 20.

In the exemplary embodiment schematically shown in FIG. 4, the electrical conductor element 22 is formed as a coil or antenna 25. This antenna 25 is electrically insulated from the electrode 18. It is conceivable that this antenna 25 is etched into the electrode 18 or is written by a laser in the material of the electrode 18 or is applied as an antenna plate to the electrode 18. Similarly, it is conceivable that the antenna 25 is stamped onto the surface of the electrode 18. Various items of information may be stored on the antenna 25 by corresponding structuring of the antenna 25. These items of information can be, for example, the type and the quality, the model, an identification number, and an area of application. A coil or an antenna 26 is associated with the distal end of the electrode carrier 15 for reading out or exciting this antenna 25. This antenna 26 is in turn connected to the generator 20. An excitation signal 27 can be generated via the control unit of the generator 20 by means of the antenna 26. This excitation signal 27 is received by the antenna 25 and emitted again as an outgoing signal 28. This outgoing signal 28 is individual and can contain the above-mentioned items of information. The outgoing signal 28 can be received and read out either by the antenna 26 or by a corresponding receiving unit in the generator 20.

The antenna 26 can be, for example, a chipless RFID component. Alternatively, it is also conceivable that an RFID component having a chip, that is to say having a data carrier, is used. The use of a chipless RFID component is particularly advantageous since the structural size is very small and a sufficient amount of data can be stored to be able to unambiguously identify the electrode 18.

A further exemplary embodiment of a method for recognizing the electrode 18 is shown in FIG. 5. An electromagnetic pulse 29 or a pulse sequence consisting of multiple pulses 29 is generated by the generator 20 or the control unit, which is applied to the electrical conductor element 22 according to FIG. 2. This pulse 29 is incident on the conductor element 22 and is individually changed and reflected in dependence on the line structure 23. These reflected outgoing signals 28 are guided by the electrical line 21 back to the generator 20 and read out there. In this time domain reflectometry (TDR), pulses having a width of a few nanoseconds are used. The interval of these pulses 29 is sufficient so that the pulses 29 and the outgoing signals 28 do not overlap. Exemplary embodiments are conceivable in which the pulses 29 and the outgoing signals 28 are guided via different lines. This suggests itself in particular for a bipolar resectoscope 10 having a coaxial cable.

LIST OF REFERENCE NUMERALS 10 resectoscope
11 shaft
12 inner tube
13 carrier
14 optical unit
15 electrode carrier
16 slide
17 guide element
18 electrode
19 eyepiece
20 generator
21 electrical line
22 electrical conductor element
23 electrical conductor structure 24 embossing
25 antenna
26 antenna
27 excitation signal
28 outgoing signal
29 pulse

The invention claimed is:

1. A surgical tool for a handheld electrosurgical instrument comprising:
an electrical conductor element having a tool-specific electronic signature that enables an unambiguous identification of the surgical tool; and
an HF generator connected to the handheld electrosurgical instrument that includes a controller configured to generate and emit an electromagnetic pulse, wherein:
the electrical conductor element is configured to:
receive the electromagnetic pulse; and
emit the electromagnetic pulse again as an outgoing signal; and
the controller of the HF generator is configured to:
receive the outgoing signal;
apply time domain reflectometry to determine characteristic properties of the electrical conductor element of the surgical tool;
associate the characteristic properties of the electrical conductor element of the surgical tool with a specific tool;
the surgical tool is configured to be detachably coupled to the handheld electrosurgical instrument and electrically connected to the HF generator; and
a proximal end of the surgical tool is coupled to a distal end of a surgical toolholder.

2. The surgical tool as claimed in claim 1, wherein the surgical tool is designed as a bipolar tool.

3. A method for recognizing a surgical tool for a handheld electrosurgical instrument detachably coupled to the surgical tool, wherein a proximal end of the surgical tool is coupled to a distal end of a surgical toolholder and is electrically connected to an HF generator, the method comprising:
enabling an electrical conductor element with a tool-specific electronic signature to uniquely identify the surgical tool;
generating and emitting an electromagnetic pulse by the HF generator connected to the handheld electrosurgical instrument; receiving the electromagnetic pulse by the electrical conductor element; and
emitting again as an outgoing signal;
receiving the outgoing signal by the HF generator;
determining characteristic properties of the electrical conductor element by time domain reflectometry (TDR); and
associating the characteristic properties of the electrical conductor element with the surgical tool.

4. The method for recognizing the surgical tool as claimed in claim 3, wherein the outgoing signal from the electrical conductor element is analyzed and matched with tool identification data stored on a database to recognize the surgical tool.

5. The method for recognizing the surgical tool as claimed in claim 3, wherein:
the electromagnetic pulse is supplied via an electrical line to the electrical conductor element; and
the outgoing signal reflected at the electrical conductor element is received and analyzed.

6. The method for recognizing the surgical tool as claimed in claim 3, wherein:

the electromagnetic pulse is applied to a coil or an antenna of the handheld electrosurgical instrument; and an excitation signal is emitted by the coil or the antenna, which is received by the electrical conductor element and the excitation signal is emitted or reflected again.

7. The method for recognizing the surgical tool according to claim 3, wherein the electromagnetic pulse is spaced from the outgoing signal such that the electromagnetic pulse and the outgoing signal do not overlap.

8. The method for recognizing the surgical tool according to claim 5, wherein the electromagnetic pulse and the outgoing signal are emitted on separate electrical lines.

\* \* \* \* \*